United States Patent [19]

Aoyagi

[11] 4,435,416
[45] Mar. 6, 1984

[54] FUNGICIDAL AND ALGICIDAL 1-METHYL-3,4-DIHALO-5-SUBSTITUTED THIO-, SULFOXYL-, OR SULFONYL-PYRAZOLES

[75] Inventor: Edward I. Aoyagi, Petaluma, Calif.

[73] Assignee: Chevron Research Company, San Francisco, Calif.

[21] Appl. No.: 393,213

[22] Filed: Jun. 28, 1982

[51] Int. Cl.³ .................. A01N 43/56; C07D 231/18
[52] U.S. Cl. ............................... 424/273 P; 548/376
[58] Field of Search ................... 548/376; 424/273 P

*Primary Examiner*—Henry R. Jiles
*Assistant Examiner*—Kurt Briscoe
*Attorney, Agent, or Firm*—D. A. Newell; T. G. DeJonghe; S. L. Biggs

[57] ABSTRACT

Compounds of the formula:

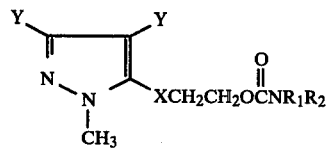

wherein Y is chloro or bromo; X is —S—, —SO— or —SO$_2$—; and R$_1$ and R$_2$ are independently hydrogen, alkyl, cycloalkyl, lower alkenyl of 3 or more carbon atoms, alkylene carbalkoxy or aryl or aralkyl optionally substituted with one or two substituents each independently selected from halogen, nitro, cyano, lower alkyl, lower alkoxy, trihalo substituted methyl and phenoxy are fungicidal and/or intermediates in the preparation of fungicides.

18 Claims, No Drawings

FUNGICIDAL AND ALGICIDAL 1-METHYL-3,4-DIHALO-5-SUBSTITUTED THIO-, SULFOXYL-, OR SULFONYL-PYRAZOLES

BACKGROUND OF THE INVENTION

This invention relates to certain novel pyrazole derivatives and their use as fungicides and algicides. In particular, I have found that the novel 1-methyl-3,4-dihalo-5 thio-, sulfinyl- and sulfonyl-pyrazoles derivatives of this invention show activity as both fungicides and algicides. In addition, the thio compounds serve as intermediates in the preparation of the corresponding sulfinyl and sulfonyl compounds.

Intermediates used in the preparation of the compounds of this invention are disclosed in my commonly-assigned U.S. patent application "Intermediates for 1-methyl-3,4-dihalo-5-substituted thio-, sulfinyl- or sulfonyl-pyrazole fungicides" Ser. No. 393,214, filed June 28, 1982.

SUMMARY OF THE INVENTION

The 1-methyl-3,4-dihalo-5-substituted thio-, sulfinyl-, or sulfonyl-pyrazole compounds of this invention are represented by the formula:

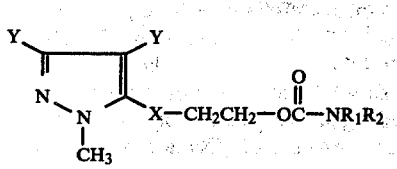

wherein Y is chloro or bromo; X is —S—, —SO—, or —SO$_2$; and R$_1$ and R$_2$ are independently hydrogen, alkyl, cycloalkyl, lower alkenyl of 3 or more carbon atoms, alkylene carbalkoxy, or aryl or aralkyl optionally substituted with one or two substituents, each independently selected from halogen, nitro, cyano, lower alkyl, lower alkoxy, trihalo-substituted methyl and phenoxy.

Among other factors, the present invention is based on my finding that the 1-methyl-3,4-dihalo-5-sulfinyl or sulfonyl substituted pyrazole compounds of this invention are surprisingly effective as fungicides and, in many cases, also as algicides. The compounds as a group are especially effective against Grape Downy Mildew, and also against Tomato Late Blight and Rice Blast.

The corresponding sulfides are useful as intermediates in the synthesis of the sulfoxides and sulfones. In addition, some of the sulfides show fungicidal and/or algicidal activities.

The trihalo and hydroxyethyl intermediates used in the synthesis of the compounds of this invention is disclosed in my commonly-assigned and copening patent application "Intermediates for 1-methyl-3,4-dihalo-5-substiuted thio-, sulfinyl-sulfonyl-pyrazole fungicides."

Representative R$_1$ and R$_2$ groups include methyl, isopropyl, n-butyl, isobutyl, tert-butyl, n-hexyl, n-octyl, allyl, pent-3-yl, phenyl, p-chlorophenyl, 3,4-dichlorophenyl, 3,5-dichlorophenyl, m-methylphenyl, p-methoxyphenyl, m-methoxyphenyl, p-butylphenyl, m-trifluoromethylphenyl, m-phenoxyphenyl, methylenecarbethoxy and cyclohexyl.

Preferred are compounds where X is —SO$_2$— and R$_1$ is alkyl, cycloalkyl, alkenyl of 3 to 6 carbon atoms, phenyl or substituted phenyl and R$_2$ is hydrogen. Particularly preferred substituted phenyl R$_1$ groups include those substituted with one to three substituents selected from halogen, lower alkyl, lower alkoxy, trihalo-substituted methyl and phenoxy.

Representative compounds of this invention are included in Table I.

Definitions

As used herein, the following terms have the following meanings, unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "alkylene" refers to the group —(CH$_2$)$_m$— wherein m is an integer greater than zero. Typical alkylene groups include methylene, ethylene, propylene and the like.

The term "alkenyl" refers to unsaturated alkyl groups having a double bond [e.g., CH$_3$CH=CH(CH$_2$)$_2$] and includes both straight- and branched-chain alkenyl groups. "Lower alkenyl" refers to groups having a total of from 3 to 6 carbon atoms. Typical lower alkenyl groups include, for example, propenyl, but-3-enyl, hex-4-enyl, 2-methyl-pent-4-enyl, and the like.

The term "halo" or "halogen" refers to the groups fluoro, chloro, bromo and iodo.

The term "alkoxy" refers to the group R'O— wherein R' is alkyl. The term "lower alkoxy" refers to alkoxy groups having from 1 to 6 carbon atoms; examples include methoxy, ethoxy, hexoxy, and the like.

The term "hydroxy alkyl" refers to the group —R'-'OH wherein R'' is branched or unbranched alkylene and the hydroxyl can be on a primary, secondary or a tertiary carbon. Examples include hydroxy ethyl and 2-hydroxypropyl and 2-hydroxy-2-methyl butyl.

The term "aryl" refers to aryl groups having from 6 to 10 carbon atoms and includes, for example, phenyl, p-chlorophenyl, m-methylphenyl, p-butylphenyl, and m-trifluoromethylphenyl.

The term "aralkyl" refers to an alkyl group of 1 to 4 carbons substituted with an aryl group of from 6 to 10 carbons and includes, for example, benzyl, p-chlorobenzyl, p-methylbenzyl and 2-phenylethyl.

The term "alkylene carbalkoxy" refers to the group

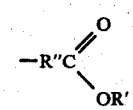

wherein R' is alkyl and R'' is alkylene.

Examples include carbethoxy methyl and carbmethoxy ethyl.

DETAILED DESCRIPTION OF THE INVENTION

The compounds of this invention may be prepared according to the following reaction sequences:

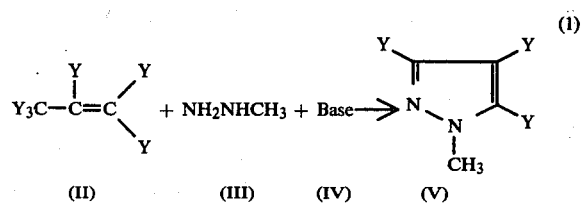

(II)  (III)  (IV)  (V)

wherein Y is chloro or bromo.

Reaction (1) is carried out by reacting (II) and (III) in the presence of base (IV). Suitable bases include organic or inorganic bases, such as $K_2CO_3$, $Na_2CO_3$, triethylamine and the like. It is preferred to add an excess of (III) and (IV) per equivalent of (II) for ease of workup. It is especially preferred to add at least 3 and more preferably 5 equivalents of (IV) per equivalent of (II). Reaction (1) may be carried out by adding (IV) with stirring to a solution of (II) and solvent, followed by the slow addition of (III). For convenience, the reaction is carried out at ambient pressure. Suitable solvents include inert organic solvents such as toluene, benzene, dimethoxyethane, tetrahydrofuran and the like. The Product (V), a low-melting white solid, is isolated by conventional procedures such as extraction, chromatography, and recrystallization.

The hydroxyethylthio intermediate used in the synthesis of the compounds of this invention is made according to the following reaction sequence.

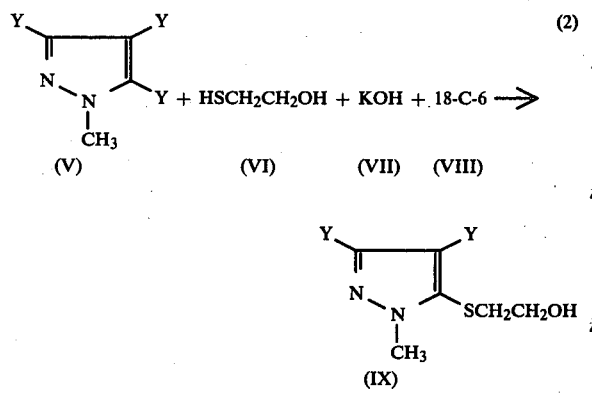

(V)  (VI)  (VII)  (VIII)

(IX)

wherein Y is as previously defined.

Both compounds of formulas (V) and (IX) are disclosed in my commonly-assigned patent application "Intermediates for 1-methyl-3,4-dihalo-5-substituted-thio-, sulfinyl- or sulfoxyl-pyrazoles fungicides".

Reaction (2) is carried out by adding (V) to (VII) and (VI) in DMSO (dimethyl sulfoxide) and heating the resulting mixture for about 1 to about 24 hours. A catalytic amount of crown ether (18-crown-6) (VIII) may be used to facilitate the reaction. Reaction (2) may also be carried out in solvents such as DMF (dimethyl formamide) and HMPA (hexamethyl phosphoramide). Water is added to the reaction mixture, and Product (IX) is isolated by conventional techniques such as extraction, filtration, chromatography, or distillation.

The sulfide compounds of Formula I, wherein $R_2$ is hydrogen, are made from the hydroxyethyl-substituted compound (IX) according to the following reaction sequence:

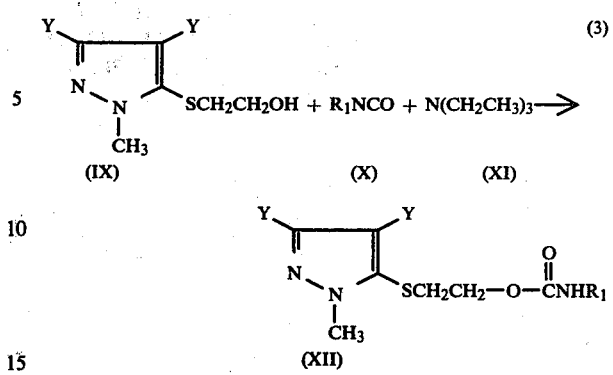

(IX)  (X)  (XI)

(XII)

wherein $R_1$ is as defined in conjunction with Formula (I). The isocyanate compounds (X) used in synthesizing (XII) are produced by methods well known to those skilled in the art.

Reaction (3) is conducted by stirring (IX), (X), and a few drops of (XI) in methylene chloride (dichloromethane) for about ½ to about 24 hours. Alternatively, after addition of the reactants, the reaction mixture may be refluxed for about ½ hour to about 24 hours. Product (XII) is isolated by conventional procedures or a combination thereof such as extraction, filtration, chromatography, recrystallization, and the like.

The sulfide compounds of Formula I wherein $R_2$ is not hydrogen are made from the hydroxyethyl-substituted compound of (IX) according to the following reaction sequence:

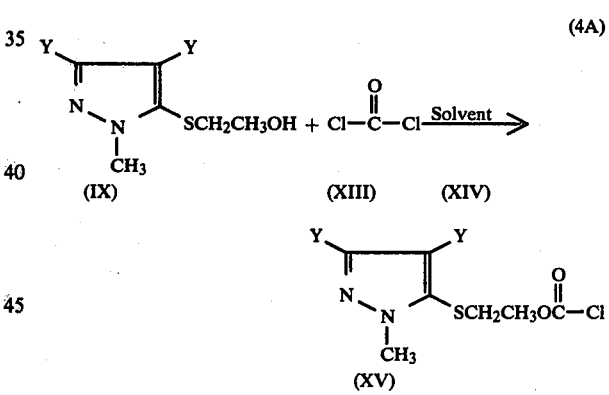

(IX)  (XIII)  (XIV)

(XV)

(XV)  (XVI)  (XVII)

(XII)

Reaction (4A) is conducted by the dropwise addition of a solution of (IX) dissolved in (XIV) to (XIII) also dissolved in solvent followed by prolonged stirring (from about 2 to about 24 hours), to give (XV). Suitable solvents (XVI) include inert organic solvents such as toluene, methylene chloride, chloroform and the like. Product XV may be used in Reaction (4B) without further isolation.

Reaction (4B) is conducted by adding (XVI) to a stirred solution of (XV) in (XVII). The reaction mixture is then stirred from about 1 to about 24 hours. Product (XII) is then isolated by conventional procedures, or a combination thereof, such as extraction, chromatography and the like.

The sulfinyl or sulfonyl compounds of Formula (I) corresponding to Products (XII) may be made from the sulfide compounds by selective oxidation of the thio group according to the following reaction scheme:

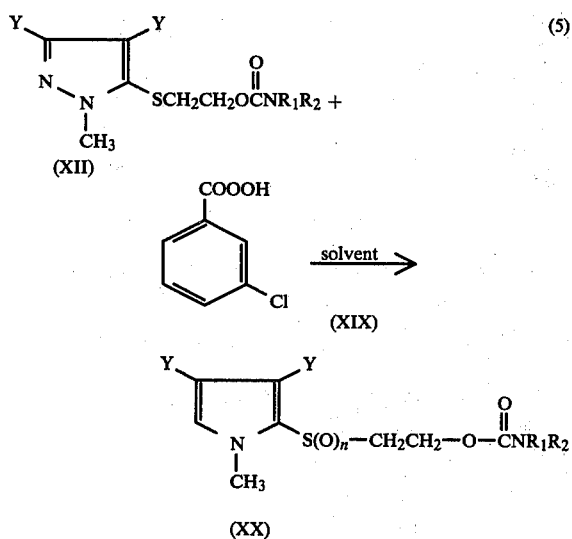

wherein n is 1 or 2 and Y, $R_1$ and $R_2$ are as previously defined.

Reaction (5) is conducted by stirring (XII) in (XIX), followed by the addition of (XVIII) in portions. The reaction mixture is stirred at ambient temperature for about 2 to about 24 hours and may optionally be refluxed for about 2 to about 8 hours. The Product (XX) is then isolated by conventional procedures such as extraction, filtration, chromatography, recrystallization, and the like. Although chloroform is the preferred solvent (XIX), other suitable solvents include other chlorinated hydrocarbon solvents such as methylene chloride and other inert organic solvents. It is well established that peroxides such as meta-chloro-perbenzoic acid (MCPBA)(XVIII) and the like oxidize thio derivatives (such as XII) to the corresponding sulfoxide or sulfone. To obtain the sulfinyl compound (n=1) corresponding to (XII), (XVIII) is added in the ratio of approximately one equivalent (XVIII) per equivalent (XII). Addition of (XVIII) in the ratio of about two or more equivalents (XVIII) per equivalent (XII) yields the corresponding sulfone.

The sulfinyl and sulfonyl compounds of this invention are useful for controlling fungi, particularly plant fungal infections and late blights, including those listed in Table II. However, some fungicidal compounds of this invention may be more fungicidally active than others against particular fungi. The sulfide compounds of this invention are used in intermediates in the synthesis of the corresponding sulfoxides and sulfones. In addition, many of the sulfide compounds of this invention exhibit fungicidal activity. However, in general, the sulfoxide and sulfone compounds exhibit a greater fungicidal activity and a wider range of fungicidal activities than the analogous sulfides. Also, the sulfonyl compounds generally exhibit greater fungicidal activity than the corresponding sulfinyl compounds.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may effect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5% to 80% fungicide, and the rest inert material, which includes dispersing agents, emulsifying agents and wetting agents. The powder may be applied to the soil as a dry dust, or preferaly as a suspension in water. Typical carriers include fuller's earth, kaolin clays, silicas, and other highly absorbent, readily wettable, inorganic, diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carriers, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

Many of the compounds of the invention are also useful for controlling microbiological organisms such as algae, bacteria, molds and occasionally aquatic weeds which foul aqueous, industrial effluents and cooling streams, such as those occurring in the paper and food processing industries. They may also be used to control such organisms in other aqueous bodies such as lakes, streams, canals, pools, and the like. When so used, a biocidal quantity of one or more of the compounds of this invention is added to the aqueous growth environment of the organisms. Usually, this dosage will range between about 0.1 to 50 ppm. In any given instance, the optimum dosage will depend upon the particular organism and aqueous body involved. For instance, when used to control algae, these compounds will usually be employed at concentrations of about 0.1 to 10 ppm. In terms of pounds of compound per acre of water one foot deep, 0.1 to 10 ppm is equal to about 0.3 to 30 pounds per acre of water one foot deep. These compounds may be applied to the aqueous growth environments of such organisms as dispersible powders or in solution with water-miscible solvents.

In addition, some of the compounds of the present invention exhibit herbicidal activity, generally in post-emergent applications. For post-emergent applications, the herbicidal compounds will be applied directly to the foliage and other plant parts. Generally, those compounds exhibiting herbicidal activity are effective against weed grasses as well as broad-leaved weeds. Some compounds may be selective with respect to the type of application and/or type of weed.

A further understanding of my invention may be had from the following non-limiting examples.

EXAMPLES

EXAMPLE 1

Preparation of 1-methyl-3,4,5-trichloro-pyrazole

To a rapidly stirred mixture of 11.4 g (0.04 mole) hexachloropropane and 16.6 g (0.012 mole) potassium carbonate in 100 ml toluene, 1.85 g (0.04 mole) methyl hydrazine was added slowly. The addition was slightly exothermic and the color of the reaction mixture turned to light orange-brown. The reaction mixture was then stirred overnight at ambient temperature. The reaction mixture was then heated to about 80° C. for about three hours and then cooled. A powdery solid appeared in the mixture. The mixture was filtered and the solids washed with ethyl ether.

The ethyl ether washings and reaction mixture filtrate were combined and stripped under reduced pressure and heat to give a black oil. The oil was chromatographed on a silica column, eluting first with hexane (which elutes unreacted starting materials) and then with methylene chloride. The methylene chloride eluate was stripped to give a pale yellow oil which solidified upon standing. Recrystallization from hexane gave 2.5 g of the product, a white solid with a melting point of 33°-35° C.

Elemental analysis for $C_4H_3Cl_3N_2$ showed: calculated %C 25.90, %H 1.63, and %N 15.11; found %C 23.67, %H 1.65, and %N 13.8.

By following the above procedure, but starting with 114 g (0.4 mole) of hexachloropropene and the corresponding proportions of the other reactants, 32.9 g of the product was prepared, a 34% yield (of theoretical).

EXAMPLE 1A

Preparation of 1-methyl-3,4,5-trichloro-pyrazole

To a stirring solution of 250 g (1 mole) of hexachloropropene in 250 ml toluene, there was added 94.4 g (2.05 moles) of methyl hydrazine dropwise. The temperature of the reaction mixture was maintained in the range of about 50° to about 60° C. by the use of external cooling. When the addition of methyl hydrazine was complete, the reaction mixture was cooled to room temperature and 276 g (2 moles) of potassium carbonate was added. The resulting mixture was carefully heated first to about 60° C., then gradually to about 85° to 90° C. Heating was carefully monitored to control occasional exotherm and degassing. After about three hours, the heat source was removed and the reaction mixture was allowed to cool to room temperature. The reaction mixture was diluted with about 500 ml ice water and extracted with methylene chloride. The organic layer (containing the product) was washed twice with water, dried over magnesium sulfate and concentrated on a rotovac to give a red oil (about 275 ml). The red oil was dissolved in hexane and filtered through a short silica column twice to give 133 g of a yellow oil which solidified. Spectra of the solid were identical to those of the product of Example 1.

EXAMPLE 2

Preparation of 1-methyl-3,4-dichloro-5-(2-hydroxyethyl)thio pyrazole

To a mixture of 26.5 g (0.34 moles) 2-mercaptoethanol, 19 g of 85% potassium hydroxide, and a few drops of 18-Crown-6 in 250 ml of DMSO, 60 g (0.32 moles) 1-methyl-3,4,5-trichloro pyrazole (product of Example 1 or 1A) were added in portions. When the addition was complete, the reaction mixture was heated to 140° C. for 1 day. The cooled reaction mixture was diluted with water and extracted with ether. The organic phase was washed four times with 200 ml water per time, dried and stripped. The crude product was chromatographed on a silica gel column. The product, 1-methyl-3,4-dichloro-5-(2-hydroxyethyl)thio pyrazole, was eluted from the column with ethyl acetate, yielding 27.7 g (37.7% yield) of a yellow oil.

Elemental analysis for $C_6H_8Cl_2N_2OS$ showed: calculated % C 31.73, % H 3.55, and % N 12.34; found % C 36.98; % H 3.77, and % N 12.60.

EXAMPLE 3

Preparation of

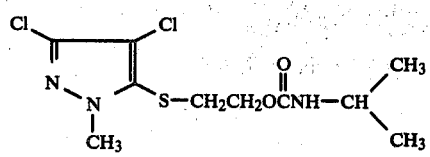

To a mixture of 7.0 g (31 mmoles) 1-methyl-3,4-dichloro-5-(2-hydroxyethyl)thio pyrazole (product of Example 2) and 5.2 g (61 mmoles) isopropyl isocyanate in 25 ml methylene chloride, a few drops (approximately 1 ml) of triethylamine were added. The resulting mixture was then refluxed for 7 hours. Solvent (methylene chloride), triethylamine, and excess isopropyl isocyanate were removed on a rotovac. The remaining material was diluted with toluene and filtered. The toluene filtered was diluted with hexane and the precipitated solid was removed by filtration. The precipitate was recrystallized from methylene chloride-hexane to give a white solid with a melting point of 58° C. to 59° C.

Elemental analysis for $C_{10}H_{15}Cl_2N_3O_2S$ showed: calculated %C 38.47, %H 4.84, and %N 13.46; found %C 39.96, %H 5.19, and %N 13.97.

EXAMPLE 4

Preparation of

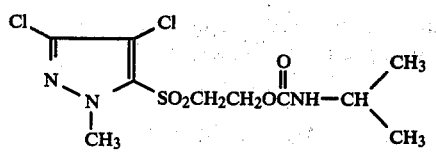

To a stirred mixture of 5 g (16 mmoles) of the product of Example 3 in 100 ml chloroform, 6.8 g (35.2 mmoles) of 90% m-chloroperoxybenzoic acid was added in portions. The reaction mixture was stirred at ambient temperature for 1 hour and then refluxed for 2 hours. An additional 3.4 g of m-chloroperoxybenzoic acid was added to the reaction mixture and the reaction mixture was refluxed for 3 hours. The reaction mixture was cooled and filtered. The filtrate was washed first with a saturated sodium carbonate solution, followed by water. The chloroform phase was dried with magnesium sulfate and stripped to give a white solid. Recrystallization of the solid from methylene chloride-hexane gave 4.5 g of a white solid with a melting point of 111° C. to 117° C.

Elemental analysis for $C_{10}H_{15}Cl_2N_3O_4S$ showed: calculated % C 34.89, % H 4.39, and % N 12.21; found % C 32.41, % H 4.64, and % N 12.58.

EXAMPLE 5

Preparation of

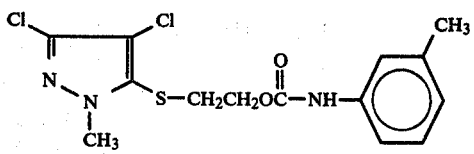

Eight grams (35 mmoles) of 1-methyl-3,4-dichloro-5-(2-hydroxyethyl)thio pyrazole (product of Example 2) and 4.7 g (135 mmoles) of m-tolylisocyanate were treated in a similar manner as in Example 3 to yield 12.6 g of white solid with a melting point of 53°–57° C.

Elemental analysis for $C_{14}H_{15}Cl_2N_3O_2S$ showed: calculated % C 46.80, % H 4.21, and % N 11.70; found % C 46.12, % H 4.46, and % N 9.66.

EXAMPLE 6

Preparation of

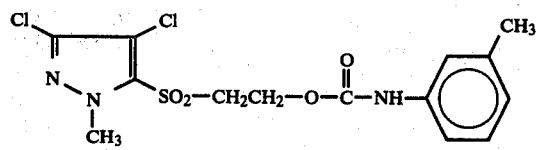

To a stirred mixture of 6.2 g (17 mmoles) of the product of Example 5 in chloroform, 7.71 g (38 mmoles) of 85% m-chloroperoxybenzoic acid was added in portions. The reaction mixture was stirred overnight. Enough additional chloroform was added to dissolve any solids. The chloroform solution was then washed first with saturated sodium carbonate, followed by water. The chloroform phase was partially concentrated and diluted with petroleum ether to precipitate the product as a light brown solid. Recrystallization of the product from methylene chloride-petroleum ether gave 6.75 g of a white solid with a melting point of 116° C. to 118° C.

Elemental analysis for $C_{14}H_{15}Cl_2N_3O_4S$ showed: calculated % C 43.00, % H 3.86, and % N 10.74; found % C 41.92, % H 4.06, and % N 9.06.

EXAMPLE 7

Preparation of

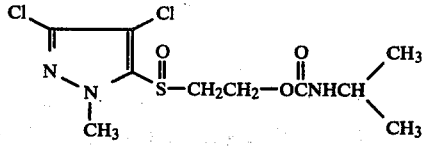

To a stirred solution of 2.1 g (6.7 mmoles) of the product of Example 3 in 50 ml of chloroform, 1.4 g (6.9 mmoles) of 85% m-chloroperbenzoic acid was added. The reaction mixture was stirred at ambient temperature for 20 hours and washed with saturated aqueous sodium bicarbonate solution. The chloroform solution was dried with magnesium sulfate. Removal of chloroform on a retovac yielded 1.6 g of viscous oil which solidified in standing.

Elemental analysis for $C_{10}H_{15}Cl_2N_3O_3S$ showed: Calculated %C 36.59, %H 4.61, %N 12.80; found %C 36.62, %H 4.76, and %N 12.95.

EXAMPLE 8

Preparation of

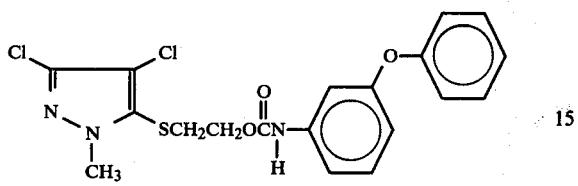

This compound was prepared from 7.0 g (38 mmoles) of 1-methyl-3,4-dichloro-5-(2-hydroxyethyl)pyrazole (product of Example 2) and 6.5 g (30.8 mmoles) of m-phenoxyphenylisocyanate in a similar manner as in Example 3. The product was purified by chromatography and isolated as an oil which solidified on standing. The yield was 8.6 g.

Elemental analysis for $C_{19}H_{17}Cl_2N_3O_3S$ showed: calculated % C 52.06, % H 3.91, and % N 9.59; found % C 51.38, % H 3.8, and % N 9.51.

EXAMPLE 9

Preparation of

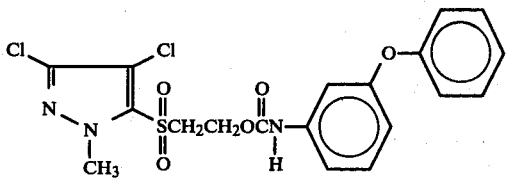

This compound was prepared by oxidation of 5.2 g (12 mmoles) of the product of Example 8 using 5.3 g (26 mmoles) of 85% m-chloroperbenzoic acid in a similar manner as in Example 6. Chromatography and recrystallization from methylene chloride-hexane gave 1.5 g of a white solid with melting point 108°-110° C.

Elemental analysis for $C_{19}H_{17}Cl_2N_3O_5S$ showed: calculated %C 48.51, %H 3.64, and %N 8.93; found %C 49.11, %H 371, and %N 9.36.

EXAMPLE 10

Preparation of

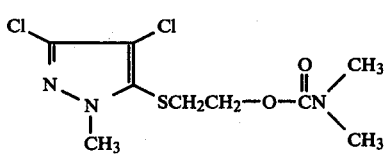

Eight grams (0.0352 mole) of 1-methyl-3,4-dichloro-5-(2-hydroxyethyl)thio pyrazole (product of Example 2) were dissolved in 50 ml toluene. The Example 2-toluene solution was added dropwise with stirring to a solution of 12.5% phosgene in toluene (containing 30.64 g (0.0352 mole) phosgene and about 245 ml toluene). The reaction mixture was stirred overnight.

Dimethylamine (1.6 g) was bubbled into the reaction mixture. The mixture was stirred overnight. After a workup such as that described in Examples 3-7, the crude product was chromatographed on silica gel to yield about 0.7 g of pure product and 3.7 g of slightly contaminated product.

Elemental analysis for $C_9H_{13}Cl_2O_2N_3S$ showed: calculated %C 36.25, %H 4.40, and %N 14.09; found %C 35.07, %H 4.51, and %N 13.01.

EXAMPLE 11

Preparation of

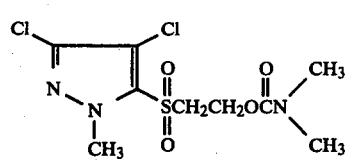

To a stirred mixture of 3.7 g of the product of Example 10, containing a small amount of impurity, in 100 ml chloroform, 7 g of 85% (0.0348 mole) of m-chloroperoxybenzoic acid was added; the resulting mixture was stirred for one day. Thin layer chromatography showed the reaction to be incomplete, so an additional 1 g of the m-chloroperoxybenzoic acid was added and the mixture stirred an additional day. The chloroform solution was then washed twice with a saturated aqueous sodium bicarbonate solution and stripped to give an oil. The oil was chromatographed on silica gel. The product eluted with 10% ethyl acetate in methylene chloride. Two grams of a viscous light yellow oil were obtained.

Elemental analysis for $C_9H_{13}Cl_2O_4N_3S$ showed: calculated %C 32.73, %H 3.97, and %N 12.73; found %C 32.82, %H 4.01, and %N 12.18.

Compounds made in a manner consistent with Examples 1 to 11 are found in Table I.

EXAMPLE 12

Mycelial Inhibition

A number of the compounds of the present invention were evaluated for in vitro fungicidal effectiveness by means of a mycelial inhibition test. This test is designed to measure the fungitoxic activity of fungicidal chemicals in terms of their degree of inhibition of mycelium growth. Fungi used were *Phythium ultimum, Rhizoctonia solani, Fusarium monilofroma, Botrytis cinerea* and *Aspargillos niger*. Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a microsprayer with the fungicidal solution. The treated paper strips were incubated at 25° C. and the data is taken after 24 hours. Fungicidal activities are measured by a zone of inhibited mycelial growth from the center of the paper strip in terms of $mg/cm^2$ needed for 99% control of the fungus ($ED_{99}$). The effectiveness of the compounds tested for fungicidal activity is reported in Table II in terms of the percent of the ED$_{99}$ of the test compound of the ED$_{99}$ of the standard Difolatan ®.

EXAMPLE 13

Grape Downy Mildew Control

The compounds of the invention were tested for the control of the Grape Downy Mildew organism *Plasmopara viticola*. Detached leaves, between 70 and 85 mm in diameter, of 7-week-old *Vitis vinifera* grape seedlings (cultivar Emperor) were used as hosts. The leaves were sprayed with a solution of the test compound in acetone. The sprayed leaves were dried, inoculated with a spore suspension of the organism, placed in a humid environmental chamber and incubated at 66° F. to 68° F. and about 100% relative humidity. After incubation for 2 days, the plants were then held in a greenhouse 7 to 9 days; then the amount of disease control was determined. The percent disease control provided by a given test compound was based on the percent disease reduction relative to untreated check plants. The results are tabulated in Table II.

EXAMPLE 14

Tomato Late Blight

Compounds of this invention were tested for the preventive control of the Tomato Late Blight organism *Phytophthora infestans*. Five- to six-week-old tomato seedlings (cultivar Bonny Best) were used. The tomato plants were sprayed with a 250 ppm suspension of the test compound in acetone, water and a small amount of a nonionic emulsifier. The sprayed plants were then inoculated 1 day later with the organism placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

EXAMPLE 15

Celery Late Blight

The Celery Late Blight tests were conducted using celery plants (Utah) 11 weeks old. The Celery Late Blight organism was *Septoria apii*. The celery plants were sprayed with solutions of the candidate toxicant (test compound) mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given candidate toxicant (test compound) is based on the percent disease reduction relative to untreated check plants. The results are reported in Table II.

EXAMPLE 16

Tomato Early Blight

Compounds of this invention were tested for the control of the Tomato Early Blight organism *Alternaria solani conida*. Tomato seedlings (variety Bonny Best) of 6 to 7 weeks old were used. The tomato plants were sprayed with a 250 ppm solution of the test compound in an acetone-and-water solution containing a small amount of nonionic emulsifier. The sprayed plants were inoculated 1 day later with the organism, placed in an environmental chamber and incubated at 66° F. to 68° F. and 100% relative humidity for 24 hours. Following the incubation, the plants were maintained in a greenhouse for about 12 days. Percent disease control provided by a given test compound was based on a comparison to the percent disease development on untreated check plants. The compounds tested and the results are tabulated in Table II.

EXAMPLE 17

Bean Rust Eradication

Compounds of this invention were tested for the eradication of Bean Rust, using 16 to 19 day old pinto bean plants. The pinto bean plants were inoculated with *Uromyces phaseoli typica* in an environmental chamber set for 100% relative humidity and 20°-21° C. After the Bean Rust has developed, one half of the plants are sprayed with solutions of the test compound in acetone. The percent disease control is determined based on the percent disease control reduction in the plants treated with test solution relative to the untreated plants. The results are tabulated in Table II.

EXAMPLE 18

Bean Powdery Mildew

The compounds of the invention were tested for control of the Bean Powdery Mildew organism *Erisiphe polygoni*. Seedling bean plants were sprayed with a 250 ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to untreated check plants. The results are tabulated in Table II.

EXAMPLE 19

Rice Blast

Compounds of this invention were tested for control of the Rice Blast organisms, *Piricularia oryzae*, using 10 to 14 day old rice plant seedlings (Calrose M-9 variety). Seedling plants were sprayed with a 625 ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on untreated check plants:

$$\% \text{ Control} = 100 \times \frac{\% \text{ disease in treated plants}}{\% \text{ disease in check}}$$

The results are tabulated in Table II.

EXAMPLE 20

Algae and Aquatic Weeds Control

Representative compounds of the invention were tested as aquatic herbicides and algicides by the following method. The weed test species were *Lemna minor* and *Elodea canadensis* and the algae used was *Spirulina maxima*.

An acetone solution of the test compound and a small amount of an alkylarylpolyoxyethylene glycol-containing surfactant was prepared. This solution was mixed with a nutrient solution in quantity sufficient to give a concentration of 2 ppm. Eight oz. plastic cups were filled with 150 ml of this solution. A sample of the test, Lemna and Elodea, was added together to each cup. Forty ml of Spirulina culture with the 2 ppm treatment was placed in 1½ oz. plastic cups or #4 glass vials. The containers were then placed in an illuminated environment and maintained at a temperature of about 20° C. for incubation. The containers were observed periodically for growth (as compared with an untreated check). The effectiveness of the test compound was determined based on a final observation of growth after 7 to 10 days. The results of the test on a 0-to-100 basis—0 indicating no effectiveness and 100 indicating complete effectiveness—are reported in Table II.

TABLE I

Compounds of the formula:

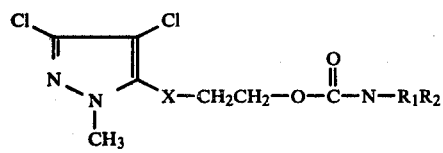

| Compound # | X | $R_1$ | $R_2$ | Physical State | % Carbon Calc. | % Carbon Found | % Hydrogen Calc. | % Hydrogen Found | % Nitrogen Calc. | % Nitrogen Found |
|---|---|---|---|---|---|---|---|---|---|---|
| 1 | —S— | —$CH_3$ | H | Tan Solid, mp 82° C. | 33.81 | 33.99 | 3.90 | 4.33 | 14.79 | 14.69 |
| 2 | —S— | —$CH(CH_3)_2$ | H | White Solid, mp 58–59° C. | 38.47 | 39.96 | 4.84 | 5.19 | 13.46 | 13.97 |
| 3 | —S— | —$(CH_2)_3CH_3$ | H | White Solid, mp 34–39° C. | 40.49 | 41.69 | 5.25 | 5.40 | 12.88 | 13.79 |
| 4 | —S— | —$C(CH_3)_3$ | H | Yellow Oil | 40.49 | 42.15 | 5.25 | 5.93 | 12.88 | 13.61 |
| 5 | —$SO_2$— | —$CH_3$ | H | White Solid, mp 116–118° C. | 30.39 | 30.52 | 5.51 | 3.57 | 13.29 | 14.77 |
| 6 | —$SO_2$— | —$CH_2CH_3$ | H | White Solid, mp 97–99° C. | 32.73 | 33.01 | 3.97 | 4.09 | 12.73 | 12.32 |
| 7 | —$SO_2$— | —$CH(CH_3)_2$ | H | White Solid, mp 111–117° C. | 34.89 | 32.41 | 4.39 | 4.64 | 12.21 | 12.58 |
| 8 | —$SO_2$— | —$(CH_2)_3CH_3$ | H | White Solid, mp 90–94° C. | 36.88 | 41.37 | 4.78 | 4.95 | 11.73 | 12.64 |
| 9 | —$SO_2$— | —$C(CH_3)_3$ | H | Very Light Yellow Viscous Oil | 36.88 | 37.11 | 4.78 | 4.84 | 11.73 | 11.51 |
| 10 | —$SO_2$— | —$(CH_2)_5CH_3$ | H | White Solid, mp 83–86° C. | 40.41 | 40.01 | 5.48 | 5.72 | 10.88 | 11.3 |
| 11 | —$SO_2$— | —$(CH_2)_7CH_3$ | H | White Solid, mp 53–60° C. | 43.48 | 44.33 | 6.08 | 5.45 | 10.14 | 7.99 |
| 12 | —SO— | —$CH(CH_3)_2$ | H | Lt Yellow Solid, mp 82–90° C. | 36.59 | 36.62 | 4.61 | 4.74 | 12.80 | 12.95 |
| 13 | —S— | —$CH_2CH=CH_2$ | H | Lt Yellow Solid, mp 44–53° C. | 38.71 | 42.5 | 4.23 | 4.81 | 13.55 | 15.32 |
| 14 | —$SO_2$— | —$CH_2CH=CH_2$ | H | White Solid, mp 68–77° C. | 35.09 | 37.43 | 3.83 | 4.17 | 12.28 | 13.39 |
| 15 | —S— | (thiophene ring) | H | White Solid, mp 104–107° C. | 44.32 | 44.54 | 5.44 | 5.56 | 11.93 | 11.70 |
| 16 | —$SO_2$— | (thiophene ring) | H | White Solid, mp 147–149° C. | 40.63 | 40.86 | 4.99 | 5.10 | 10.93 | 10.96 |
| 17 | —S— | —$CH_2C(=O)OCH_2CH_3$ | H | Off-white Solid, mp 44–48° C. | 37.08 | 37.94 | 4.24 | 4.32 | 11.80 | 12.49 |
| 18 | —$SO_2$— | —$CH_2C(=O)OCH_2CH_3$ | H | Off-white Solid, mp 125–126° C. | 34.03 | 33.10 | 3.90 | 3.65 | 10.82 | 10.42 |
| 19 | —S— | (2,4-dichlorophenyl) | H | White Solid, mp 105–108° C. | 37.61 | 38.17 | 2.67 | 3.06 | 10.12 | 15.85 |

TABLE I-continued

Compounds of the formula:

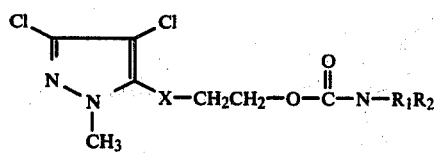

| Compound # | X | R₁ | R₂ | Physical State | % Carbon Calc. | % Carbon Found | % Hydrogen Calc. | % Hydrogen Found | % Nitrogen Calc. | % Nitrogen Found |
|---|---|---|---|---|---|---|---|---|---|---|
| 20 | —S— | phenyl-CH₃ | H | White Solid, mp 53–57° C. | 46.80 | 46.12 | 4.21 | 4.46 | 11.70 | 9.66 |
| 21 | —S— | phenyl-(CH₂)₃CH₃ | H | Off-white Solid, mp 55–58° C. | 50.77 | 50.70 | 5.26 | 5.59 | 10.45 | 10.46 |
| 22 | —S— | phenyl-OCH₃ | H | Yellow Very Viscous Oil | 44.81 | 43.95 | 4.03 | 4.05 | 11.20 | 10.78 |
| 23 | —S— | phenyl-CF₃ | H | Pink-white Solid, mp 61–66° C. | 40.58 | 40.83 | 2.92 | 2.9 | 10.14 | 10.22 |
| 24 | —S— | phenyl-O-phenyl | H | Off-white Solid, mp 104–119° C. | 52.06 | 51.38 | 3.91 | 3.80 | 9.59 | 9.51 |
| 25 | —SO— | phenyl-CH₃ | H | Off-white Solid, mp 95–101° C. | 44.45 | 44.27 | 4.03 | 4.07 | 11.20 | 10.92 |
| 26 | —SO₂— | phenyl | H | White Solid, mp 120–122° C. | 41.28 | 42.39 | 3.47 | 3.64 | 11.11 | 11.80 |
| 27 | —SO₂— | phenyl-Cl | H | White Solid, mp 150–152° C. | 37.84 | 37.81 | 2.93 | 2.87 | 10.18 | 9.55 |
| 28 | —SO₂— | phenyl-Cl,Cl | H | White Solid, mp 197–204° C. | 34.92 | 33.5 | 2.48 | 2.56 | 9.40 | 9.04 |
| 29 | —SO₂— | phenyl-Cl,Cl | H | White Solid, mp 162–165° C. | 34.92 | 33.68 | 2.48 | 2.67 | 9.40 | 9.14 |
| 30 | —SO₂— | phenyl-CH₃ | H | White Solid, mp 116–118° C. | 43.00 | 41.92 | 3.86 | 4.06 | 10.74 | 9.06 |
| 31 | —SO₂— | phenyl-(CH₂)₃CH₃ | H | Tan Solid, mp 117–118° C. | 47.03 | 46.86 | 4.88 | 4.81 | 9.68 | 9.91 |
| 32 | —SO₂— | phenyl-OCH₃ | H | Tan Solid, mp 105–109° C. | 41.29 | 42.03 | 3.71 | 3.85 | 10.32 | 10.39 |

TABLE I-continued

Compounds of the formula:

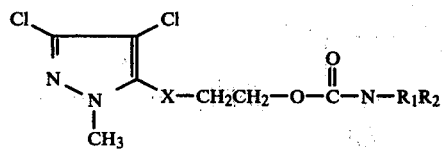

| Compound # | X | R₁ | R₂ | Physical State | % Carbon Calc. | % Carbon Found | % Hydrogen Calc. | % Hydrogen Found | % Nitrogen Calc. | % Nitrogen Found |
|---|---|---|---|---|---|---|---|---|---|---|
| 33 | —SO₂— | —C₆H₄—OCH₃ | H | White Solid, mp 153–155° C. | 41.29 | 40.35 | 3.71 | 3.96 | 10.32 | 10.29 |
| 34 | —SO₂— | —C₆H₄—CF₃ | H | White Solid, mp 109–115° C. | 37.68 | 40.31 | 2.71 | 2.83 | 9.42 | 7.68 |
| 35 | —SO₂— | —C₆H₄—O—C₆H₅ | H | White Solid, mp 108–110° C. | 48.51 | 49.11 | 3.64 | 3.71 | 8.93 | 9.36 |
| 36 | —S— | —C₆H₄—O—C₆H₅ | H | Tan Solid, mp 93–96° C. | 52.06 | 52.43 | 3.91 | 4.16 | 9.51 | 9.64 |
| 37 | —SO₂— | —C₆H₄—O—C₆H₅ | H | White Solid, mp 129–133° C. | 48.52 | 48.87 | 3.64 | 3.68 | 8.93 | 9.09 |
| 38 | —SO₂— | —CH₂CH₂CH₃ | H | White Solid, mp 83–93° C. | 34.89 | 34.78 | 4.39 | 4.24 | 12.21 | 11.09 |
| 39 | —S— | —CH₃ | —CH₃ | Yellow Oil | 36.25 | 35.07 | 4.40 | 4.51 | 14.09 | 13.01 |
| 40 | —SO₂— | —CH₃ | —CH₃ | Lt Yellow Solidified | 32.73 | 32.82 | 3.97 | 4.01 | 12.73 | 12.18 |

TABLE II

| Compound # | Pythium | Rhizoctonia | Fusarium | Botrytis | Asper. | Grape Downy Mildew | Tomato Late Blight | Celery Late Blight | Tomato Early Blight | Bean Rust Erad | Bean Powdery Mildew | Rice Blast |
|---|---|---|---|---|---|---|---|---|---|---|---|---|
| 1 | 0 | 0 | 0 | 33 | 0 | 0 | 14 | 0 | 23 | 0 | 0 | |
| 2 | 0 | 0 | 0 | | 0 | 64 | 0 | | 0 | 11 | 0 | |
| 3 | 0 | 0 | 0 | 0 | 0 | 31 | 12 | | 6 | 4 | 0 | 13 |
| 4 | 0 | 0 | 0 | | 0 | 15 | 54 | 9 | 67 | | | 0 |
| 5 | 0 | 0 | 0 | 0 | 0 | 100 | 84 | 79 | 83 | 0 | 13 | |
| 6 | 0 | 0 | 0 | 0 | 0 | 17 | 8 | 0 | 4 | 0 | 0 | |
| 7 | 0 | 43 | 0 | 0 | 0 | 100 | 97 | | 4 | 0 | 33 | |
| 8 | 0 | 0 | 0 | | 0 | 100 | 100 | 100 | 89 | | | 94 |
| 9 | 13 | 0 | 0 | | 0 | 95 | 93 | 55 | 67 | | | 88 |
| 10 | 0 | 0 | 0 | 0 | 0 | 97 | 100 | 87 | 21 | 0 | 0 | 64 |
| 11 | 0 | 0 | 0 | 0 | 0 | 100 | 95 | | 22 | 79 | 0 | 75 |
| 12 | 0 | 0 | 0 | 0 | 0 | 67 | 75 | 0 | 14 | 0 | 0 | 0 |
| 13 | 0 | 0 | 0 | 0 | 0 | 6 | 0 | 27 | 0 | 0 | 0 | 0 |
| 14 | 0 | 0 | 0 | 0 | 0 | 61 | 97 | 73 | 0 | 0 | 0 | 89 |
| 15 | 0 | 0 | 0 | 0 | 0 | 8 | 0 | — | 44 | 21 | 0 | 0 |
| 16 | 0 | 0 | 0 | 0 | 0 | 100 | 96 | — | 50 | 46 | 0 | 94 |
| 17 | 0 | 0 | 0 | 0 | 0 | 14 | 0 | 6 | 21 | 0 | 0 | |
| 18 | 0 | 50 | 29 | 0 | 0 | 59 | 10 | 56 | 36 | 0 | 0 | |
| 19 | 0 | 0 | 0 | 0 | 0 | 97 | 62 | 0 | 17 | 0 | 23 | |
| 20 | 0 | 0 | 0 | 0 | 0 | 100 | 50 | 0 | 10 | 0 | 23 | |
| 21 | | 0 | 0 | 0 | 0 | 6 | 0 | 55 | | 0 | 8 | 0 |
| 22 | 0 | 0 | 0 | 0 | 0 | 85 | 31 | 79 | 0 | 0 | 0 | 59 |
| 23 | 0 | 0 | 0 | 0 | 0 | 40 | 44 | 48 | 18 | 0 | 0 | 0 |
| 24 | 0 | 0 | 0 | 0 | 0 | 39 | 20 | 0 | 18 | 0 | 3 | 25 |
| 25 | 0 | 0 | 0 | 0 | 0 | 42 | 15 | 0 | 0 | 0 | 0 | 0 |
| 26 | 21 | 16 | 52 | | 59 | 100 | 97 | 82 | 100 | | | 63 |
| 27 | 0 | 59 | 28 | | 18 | 100 | 97 | | 74 | 0 | 0 | |
| 28 | 0 | 25 | 0 | 0 | 0 | 100 | 76 | 14 | 83 | 0 | 23 | |
| 29 | 0 | 56 | 43 | 28 | 0 | 100 | 96 | 0 | 68 | 0 | 0 | |
| 30 | 16 | 56 | 54 | 33 | 50 | 100 | 96 | 76 | 59 | 0 | 0 | |
| 31 | | 0 | 0 | 0 | 0 | 100 | 97 | 50 | | 0 | 12 | 56 |
| 32 | 17 | 0 | 0 | 0 | 0 | 100 | 75 | 95 | 50 | 0 | 0 | |

TABLE II-continued

| Compound # | Phy-thium | Rhizoc-tonia | Fusa-rium | Botrytis | Asper. | Grape Downy Mildew | Tomato Late Blight | Celery Late Blight | Tomato Early Blight | Bean Rust Erad | Bean Powdery Mildew | Rice Blast |
|---|---|---|---|---|---|---|---|---|---|---|---|---|
| 33 | 0 | 16 | 24 | 28 | 17 | 100 | 76 | 44 | 83 | 0 | 0 | |
| 34 | 0 | 9 | 0 | 0 | 0 | 97 | 68 | 79 | 23 | 0 | 0 | 93 |
| 35 | 0 | 0 | 0 | 38 | 100 | 100 | 97 | 80 | 27 | 0 | 3 | |
| 36 | 0 | 0 | 0 | 0 | 0 | 52 | 7 | — | 0 | 0 | 18 | 17 |
| 37 | 0 | 0 | 0 | 45 | 0 | 95 | 86 | — | 14 | 0 | 0 | 25 |
| 38 | 0 | 0 | 0 | 28 | 0 | 86 | 11 | — | 0 | 0 | 0 | 58 |
| 39 | 0 | 0 | 0 | 0 | 0 | 79 | 0 | 0 | 0 | 0 | 0 | 0 |
| 40 | 0 | 0 | 0 | 0 | 0 | 45 | 0 | 0 | 0 | 0 | 25 | 67 |

TABLE III

| Compound # | Percent Aquatic Weed Control | | |
|---|---|---|---|
| | Spirulina | Lemna | Elodea |
| 1 | 0 | 0 | 0 |
| 2 | 0 | 0 | 0 |
| 3 | 0 | 0 | 60 |
| 4 | 0 | 0 | 0 |
| 5 | 60 | 70 | 70 |
| 6 | 50 | 95 | 100 |
| 7 | 90 | 35 | 60 |
| 8 | 97 | 45 | 70 |
| 9 | 95 | 0 | 0 |
| 10 | 98 | 95 | 90 |
| 11 | 0 | 0 | 0 |
| 12 | 0 | 0 | 0 |
| 13 | 0 | 0 | 75 |
| 14 | 98 | 95 | 75 |
| 15 | 0 | 0 | 0 |
| 16 | 0 | 0 | 0 |
| 17 | 0 | 0 | 50 |
| 18 | 90 | 0 | 0 |
| 19 | 35 | 0 | 0 |
| 20 | 0 | 0 | 0 |
| 21 | 0 | 0 | 0 |
| 22 | 0 | 0 | 0 |
| 23 | 0 | 0 | 0 |
| 24 | 0 | 0 | 0 |
| 25 | 0 | 0 | 0 |
| 26 | 98 | 80 | 70 |
| 27 | 90 | 80 | 90 |
| 28 | 0 | 0 | 0 |
| 29 | 95 | 0 | 0 |
| 30 | 98 | 0 | 60 |
| 31 | 95 | 0 | 0 |
| 32 | 90 | 0 | 35 |
| 33 | 60 | 30 | 80 |
| 34 | 90 | 0 | 0 |
| 35 | 0 | 0 | 0 |
| 36 | 0 | 0 | 0 |
| 37 | 100 | 0 | 0 |
| 38 | 100 | 80 | 65 |
| 39 | — | — | — |
| 40 | 80 | 75 | 85 |

What is claimed is:

1. A compound of the formula:

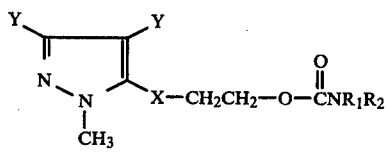

wherein Y is chloro or bromo; X is —S—, —SO—, or —SO₂—; and R₁ and R₂ are independently hydrogen, alkyl having from 1 to 8 carbon atoms, cycloalkyl having up to 6 carbon atoms, lower alkenyl of 3 to 6 carbon atoms, alkylene carbalkoxy having a total of 3 to 4 carbon atoms, or aryl or aralkyl having from 6 to 10 carbon atoms optionally substituted with one or two substituents, each independently selected from the group consisting of halogen, nitro, cyano, lower alkyl having from 1 to 6 carbon atoms, lower alkoxy having from 1 to 6 carbon atoms, trihalo-substituted methyl and phenoxy.

2. A compound according to claim 1, wherein R₂ is hydrogen and Y is chloro.

3. A compound according to claim 2 wherein X is —SO₂—.

4. A compound according to claim 3 wherein R₁ is —CH(CH₃)₂.

5. A compound according to claim 3 wherein R₁ is

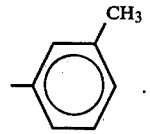

6. A compound according to claim 3 wherein R₁ is phenyl.

7. A method for controlling fungi which comprises contacting said fungi or their growth environment with a fungicidally effective amount of a compound of the formula defined in claim 1.

8. A method for controlling fungi which comprises contacting said fungi or their growth environment with a fungicidally effective amount of a compound of the formula defined in claim 2.

9. A method for controlling fungi which comprises contacting said fungi or their growth environment with fungicidally effective amount of a compound of claim 3.

10. A method for controlling fungi which comprises contacting said fungi or their growth environment with a fungicidally effective amount of the compound of claim 4.

11. A method according to claim 10 wherein the fungus is Rice Blast.

12. A method according to claim 10 wherein the fungus is Grape Downy Mildew.

13. A method of controlling fungi which comprises contacting said fungi or their growth medium with a fungicidally effective amount of the compound of claim 5.

14. A method according to claim 13 wherein the fungus is Rice Blast.

15. A method according to claim 13 wherein the fungus is Grape Downy Mildew.

16. A method of controlling fungi which comprises contacting said fungi or their growth medium with a fungicidally effective amount of the compound of claim 6.

17. A compound according to claim 3 wherein R₁ is —(CH₂)₅CH₃.

18. A method of controlling fungi which comprises contacting said fungi or their growth medium with a fungicidally effective amount of the compound of claim 17.

* * * * *